United States Patent [19]

MacKenzie

[11] Patent Number: 4,614,189
[45] Date of Patent: Sep. 30, 1986

[54] FACIAL TREATMENT MASK

[76] Inventor: Virginia B. MacKenzie, 1520 W. Horseshoe Bend, Rochester, Mich. 48064

[21] Appl. No.: 646,776

[22] Filed: Sep. 4, 1984

[51] Int. Cl.[4] .......................... A61F 7/08; A61F 7/10
[52] U.S. Cl. .................................. 128/380; 128/402; 128/403; 128/DIG. 15
[58] Field of Search ........ 128/380, 402, 403, DIG. 15

[56] References Cited

U.S. PATENT DOCUMENTS

| | | | |
|---|---|---|---|
| 702,759 | 6/1902 | Allegretti | 128/402 |
| 1,322,984 | 11/1919 | Wesley | 128/402 |
| 1,480,780 | 1/1924 | Pauley | 128/402 |
| 1,522,295 | 1/1925 | Gee | 128/402 |
| 2,477,883 | 8/1949 | Lefohn | 128/402 |
| 2,562,121 | 7/1951 | Poux | 128/402 X |
| 3,541,608 | 3/1969 | Otwell | 128/DIG. 15 X |

Primary Examiner—Anton O. Oechsle
Attorney, Agent, or Firm—Gifford, Groh, VanOphem, Sheridan, Sprinkle & Dolgorukov

[57] ABSTRACT

A thermal mask for treating various medical conditions of the facial area involving the application of either heat or cold. The facial mask is constructed of a lightweight and soft material designed to conform to the facial contours. The mask generally comprises a fluid reservoir with a pair of eye holes and a notch for accepting the bridge of the nose. A port or opening with a seal or plug is located at the top of the mask for filling or emptying the reservoir. The mask is held in place by a series of straps which are provided with adhesive material to detachably mount the mask to the user's head. The reservoir of the mask may be filled with hot or cold water, or ice, depending on its intended use.

4 Claims, 3 Drawing Figures

4,614,189

FACIAL TREATMENT MASK

FIELD OF THE INVENTION

This invention relates to a device for treating medical conditions of the facial area and, in particular, to a treatment mask which may be utilized to apply heat or cold to key facial areas.

DESCRIPTION OF THE PRIOR ART

Thousands of people suffer from various medical conditions affecting the facial area, particularly the sinus cavities. Many more are affected by contusions or swelling due to trauma or dental surgery. Generally, these conditions are treated by medication prescribed by a medical practitioner or purchased through a pharmacy. However, because many of these conditions of the facial area involed infection or swelling, it may also be desirable to apply heat or cold.

The simplest of the past known devices is the hot water bottle which may be filled with hot or cold water and applied to the face. These water bottles are generally quite large and have a defined shape which limits their usefulness when it is desired to apply the bottle in close contact with the sinus cavities of the face. Moreover, the user is generally immobilized while using the hot water bottle since no means are provided for retaining the bottole against the face and, when in place, the bottle obstructs the user's vision.

Other known facial treatment packs are provided with straps to hold the pack against the face. However, these devices generally comprise a rigid fluid reservoir which does not readily conform to the contours of the face. Since it is desirable to place the treatment pack in close contact to the face to provide effective treatment, these rigid devices provide only isolated effectiveness. The rigid construction of these treatment packs stems from the inclusion of a spout for filling and emptying the fluid reservoir. Generally, the spout comprises a rigid cylindrical opening which can be sealed by a similarly shaped plug.

Still other known treatment masks comprise a pliable reservoir which is filled with chemical substance capable of retaining heat or cold. These masks are generally provided with nose and eye holes so that they can closely conform to the face. However, these devices have limited usefulness because the chemical substance inside the mask tends to assume room temperature thereby losing its effectiveness. In order to regain the proper effectiveness, the mask must be stored in a freezer or heated prior to reapplying the mask.

SUMMARY OF THE PRESENT INVENTION

The present invention overcomes the disadvantages of the prior art by providing a facial treatment mask which may be utilized to apply heat or cold to the facial area while permitting the user to continue most normal activities.

The treatment mask according to the present invention comprises a pliable fluid reservoir with a top and two side straps to hold the mask in the proper position on the user's face. The straps are provided with an adhesive material so that the ends of the straps may be joined at the back of the head. Two eye holes are formed through the reservoir to avoid obstructing the user's eyesight. Additionally, a notch is formed in the bottom portion of the reservoir which rests on the bridge of the nose. Finally, a fluid port is provided at the top of the reservoir to facilitate filling or emptying the mask as desired. The fluid port preferably comprises a threaded cylinder which can be sealed by a threaded plug or stopper.

Prior to application, the mask is filled with hot or cold water depending on the intended use. Alternatively, the mask could be filled with crushed ice for increased effectiveness. In either case, the fluid port is sufficiently wide and rigid to perit simple filling of the reservoir of the mask. Once filled, the pliable construction of the mask allows it to be applied to the face in close contact with the contours of the face. This is particularly important when treating sinus ailments which require heat treatments applied as close as possible to the sinus cavities.

Other objects, features and advantages of the invention will be apparent from the following detailed description taken in connection with the accompanying drawings.

BRIEF DESCRIPTION OF THE DRAWING

The present invention will be more fully understood by reference to the following detailed description of the preferred embodiment of the present invention when read in conjunction with the accompanying drawing, in which like reference characters refer to like parts throughout the views, and in which.

DETAILED DESCRIPTION OF THE PREFERRED EMBODIMENT

Figure 1:
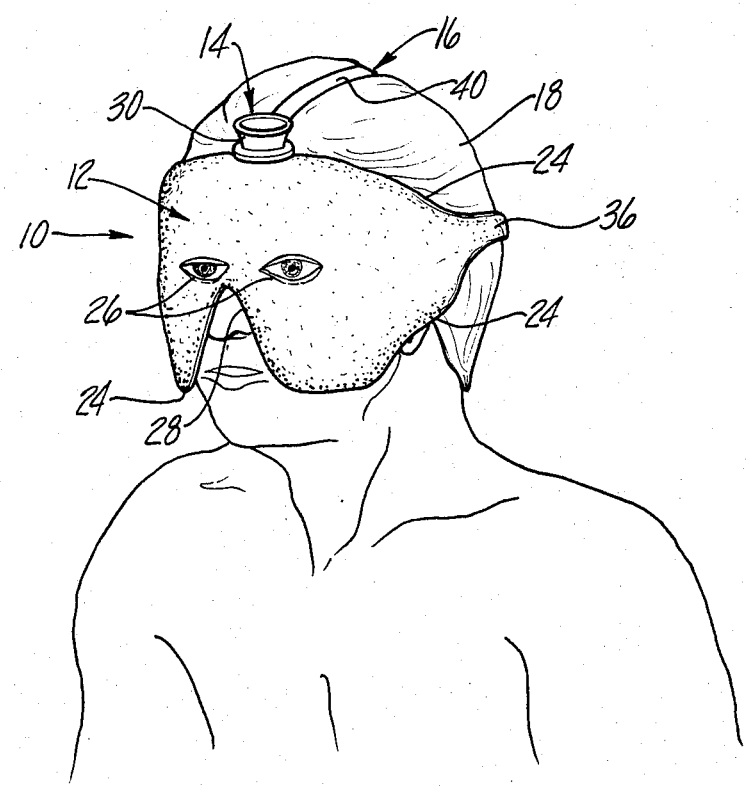
FIG. 1 is a front perspective view of the preferred embodiment of the present invention applied to the facial area of a user.
Figure 2:
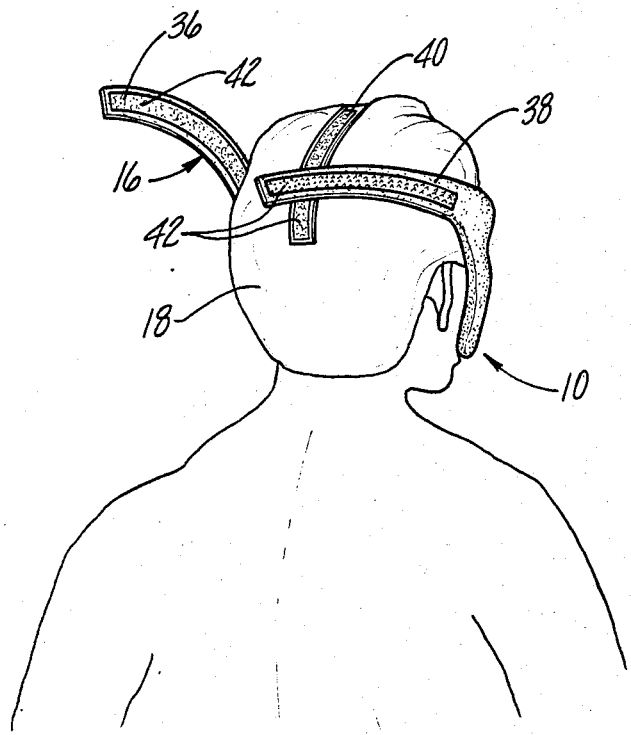
FIG. 2 is a rear perspective view of the present invention mounted to the head of a user.
Figure 3:
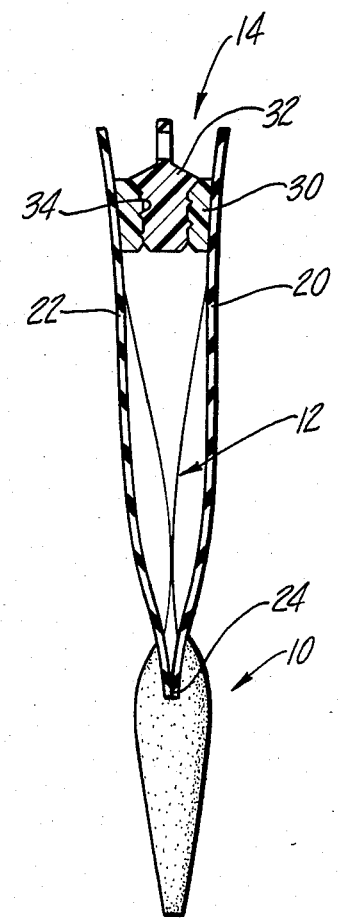
FIG. 3 is a cross-sectional view of the present invention.

Referring generally to FIGS. 1 through 3, there is shown a facial treatment mask 10 embodying the present invention and comprising a fluid reservoir 12, an annular port 14 for filling the reservoir 12, and means 16 for mounting the mask to a user's head 18. The mask 10 is designed to be applied to the facial area of the user's head 18 such that the mask 10 conforms to the contours of the face.

As is best shown in FIG. 3, the fluid reservoir 12 comprises an inner wall 20 and an outer wall 22. The walls 20 and 22 are preferably sealingly engaged at their edge 24. However, it is to be understood that the fluid reservoir 12 can have a one-piece construction with no engaging seams. Referring now to FIG. 1, the reservoir 12 has an irregular but substantially elliptical shape. A pair of eye holes 26 are provided through the reservoir 12 with inner wall 20 and outer wall 22 sealingly engaged around the edges of the eye holes 26. In addition, a V-shaped notch 28 is provided for the user's nose. The notch 28 is adapted to fit over the bridge of the nose thereby providing added support for the mask 10. Alternatively, a triangular opening may be provided for the nose thereby extending the lower edge of the mask 10.

Referring to FIGS. 1 and 3, the annular port 14 preferably comprises a rigid cylinder 30 sealingly secured to walls 20 and 22. A cylindrical plug or stopper 32 seals the port 14 and the reservoir 12. Both the cylinder 30 and the stopper 32 are provided with threads 34 so that the stopper 32 threadably engages the cylinder 30.

However, any known sealing engagement may be utilized to seal the reservoir while permitting simple filling and emptying of the reservoir 12.

In the preferred embodiment, the mounting means comprises two side straps 36 and 38 and a top strap 40. As shown in FIG. 2, the straps 36, 38 and 40 are provided with an adhesive material 42 to facilitate mounting and removing the mask 10. Still referring to FIG. 2, the adhesive material 42 is provided on the abutting faces of the straps so that, with the straps 36, 38 and 40 secured together at a common point, one strap is sandwiched in between the other two straps. Alternatively, the straps may also be provided with Velcro material for ease of adjustment and mounting. Other well known methods of attaching the ends of the straps may also be used. The straps 36, 38 and 40 are preferably an extension of the walls 20 and 22 of the reservoir 12, however, the straps could be separately secured to the reservoir 12.

The mask 10 is constructed of a pliable material such as rubber so that it conforms to the contours of the face. The mask 10 is designed to treat various medical conditions of the facial area by applying heat or cold to critical areas. In use, the reservoir 12 is first filled with either hot or cold water depending on the desired treatment. After sealing the reservoir 12 by closing the port 14, the mask 10 may be placed on the face such that the user may see through the eye holes 26 and the notch 28 is supported by the bridge of the nose. Once properly in place, the top strap 40 is placed over the top of the head 18 and the side straps 36 and 38 are wrapped around the sides of the head. All three straps 36, 38 and 40 are then secured together at the back of the head.

Thus, the present invention provides simple and convenient means of treating the facial area with hot or cold applications. By continuously replacing the fluid in the reservoir, the effectiveness of the mask is maintained for extended periods. Moreover, because the mask does not obstruct the user's vision and is relatively secure once in place, the mask may be worn while continuing normal activities. Finally, because of its pliability, the mask closely engages the facial features thereby providing effective treatment.

The foregoing detailed description has been given for clearness of understanding only and no unnecessary limitations should be understood therefrom as some modifications will be obvious to those skilled in the art.

I claim:

1. A treatment mask for applying heat or cold to the facial area, said treatment mask comprising:
   an enclosed fluid reservoir with sealingly engaged inner and outer walls wherein said reservoir has two elliptical passages which conform substantially to the shape of the human eye extending therethrough and wherein said inner and outer walls are sealingly engaged at the periphery of said passages;
   wherein said fluid reservoir includes a substantially triangular notch removed from the lower portion of said fluid reservoir and wherein said notch conforms to the bridge of the human nose whereby said mask is at least partially supported by the bridge of the nose when said mask is applied to the face;
   an annular port comprising a rigid cylinder disposed between said inner and outer walls of said fluid reservoir at the top of said reservoir;
   a plug for sealing said annular port wherein said plug and said cylinder are threaded and wherein said plug threadably engages said rigid cylinder; and
   wherein said reservoir comprises an upper edge which extends laterally outwardly from both sides of the port, said upper edge having two ends, each end being spaced from said port,
   wherein said reservoir comprises a pair of lower edges, each said lower edge sloping upwardly from a bottom of said notch and to one end of said upper edge, and
   means for detachably securing said mask to the head comprising a pair of side straps, one end of each side strap being secured to one end of said top edge, and a top strap, one end of said top strap being secured to said top edge adjacent said port,
   means for detachably securing the other ends of said straps in face abutting relationship together at a common point at the back of the head and,
   said detachable securing means including adhesive material on the abutting faces of said other ends of said straps to enable one of said ends to be releasably sandwiched in between said other two ends.

2. The treatment mask as defined in claim 1 wherein said inner and outer walls of said fluid reservoir are made of an elastic material.

3. The treatment mask as defined in claim 2 wherein said elastic material is a pliable rubber.

4. The treatment mask as defined in claim 1 wherein said one top strap extends over the top of the user's head and wherein said side straps extend around the sides of the user's head.

* * * * *